United States Patent [19]

Gilb et al.

[11] Patent Number: 5,300,693
[45] Date of Patent: Apr. 5, 1994

[54] PROCESS FOR THE PREPARATION OF 1,4-BIS(4-FLUOROBENZOYL)-BENZENE

[75] Inventors: Walter Gilb, Hofheim am Taunus; Georg Grötsch, Bad Soden am Taunus; Hans Schubert, Kelkheim, all of Fed. Rep. of Germany

[73] Assignee: Hoechst Aktiengesellschaft, Frankfurt am Main, Fed. Rep. of Germany

[21] Appl. No.: 949,526

[22] PCT Filed: May 18, 1991

[86] PCT No.: PCT/EP91/00929
§ 371 Date: Nov. 25, 1992
§ 102(e) Date: Nov. 25, 1992

[87] PCT Pub. No.: WO92/18862
PCT Pub. Date: Dec. 12, 1991

[30] Foreign Application Priority Data
May 25, 1990 [DE] Fed. Rep. of Germany ....... 4016895

[51] Int. Cl.$^5$ ............................................. C07C 45/46
[52] U.S. Cl. ..................................................... 568/323
[58] Field of Search ........................................ 568/323

[56] References Cited

U.S. PATENT DOCUMENTS 4,820,791  4/1989  Hergenrother et al. ............ 568/323

FOREIGN PATENT DOCUMENTS 0178184  4/1986  European Pat. Off. ............ 568/323
0262919  4/1988  European Pat. Off. ............ 568/323
3531837  3/1987  Fed. Rep. of Germany ...... 568/323
3806656  9/1989  Fed. Rep. of Germany ...... 568/323
3807623  9/1989  Fed. Rep. of Germany ...... 568/323

OTHER PUBLICATIONS

Patent Abstracts of Japan, Abstract of Kokai 62-103038, Oct. 15, 1987.

Primary Examiner—James H. Reamer
Attorney, Agent, or Firm—Connolly & Hutz

[57] ABSTRACT

Process for producing 1,4-bis-(4-fluorbenzoyl)-benzol by reacting terephthaloyl chloride with fluorbenzol in the presence of aluminium chloride or aluminium bromide, characterized in that aluminium chloride or aluminium bromide is added in metered quantities to a mixture of terephthaloyl chloride and fluorbenzol at temperatures of approximately 25° C. to approximately 68° C. and the mixture is allowed to react at said temperatures.

8 Claims, No Drawings

PROCESS FOR THE PREPARATION OF 1,4-BIS(4-FLUOROBENZOYL)-BENZENE

The invention relates to an improved process for the preparation of 1,4-bis(4-fluorobenzoyl)benzene in high yield and purity by reaction of terephthaloyl chloride with fluorobenzene while metering in aluminum chloride or aluminum bromide at reaction temperatures below 70° C.

1,4-Bis(4-fluorobenzoyl)benzene is a useful starting material for the preparation of high performance plastics, such as, for example, polyether ketosulfones, polyether ketones or laminated materials.

In spite of the use of novel Friedel-Crafts catalysts, such as hydrogen fluoride/boron trifluoride mixtures (DE-OS 3,806,656) or polyfluorinated alkanesulfonic acids (DE-OS 3,807,623), aluminum chloride still has great importance as a catalyst for the preparation of 1,4-bis(4-fluorobenzoyl)benzene from fluorobenzene and terephthaloyl chloride, as it is inexpensive, relatively easy to handle and has been thoroughly investigated with respect to its toxicological and ecological properties. preparation of 1,4-bis(4-fluorobenzoyl)benzene from fluorobenzene and terephthaloyl chloride in the presence of aluminum chloride is known in principle, a process for the preparation of 1,4-bis(4-chlorobenzoyl)benzene described in GB Patent 1,139,296 being referred to for experimental details In this process, excess chlorobenzene is reacted with terephthaloyl chloride and aluminum chloride in the molar ratio 13:1.0:2.3 at 130° C. (boiling temperature of chlorobenzene) in the course of 6 h. Yield and purity are not given therein The preparation of 1,4-bis(4-fluorobenzoyl)benzene from fluorobenzene and terephthaloyl chloride with the aid of AlCl3 is also described in DE-OS 3,531,837. In Example 1 therein, virtually the same molar ratios are used as in GB Patent 1,139,296 mentioned further above. However, according to Example 1 here, aluminum chloride is suspended in fluorobenzene and terephthaloyl chloride, dissolved in fluorobenzene, is then metered in, the temperature of the reaction mixture rising from 60° C. to 85° C. (boiling temperature of fluorobenzene).

In the abovementioned process of DE-OS 3,531,837, the reaction is thus at least partially carried out at the boiling temperature of fluorobenzene. However, the yield and purity given for the 1,4-bis(4-fluorobenzoyl)benzene in DE-OS 3,531,837 cannot be assessed, as after the purification more product is obtained (1250 g) than there was crude product present (1225 g.

In U.S. Pat. No. 4,820,791, J. Pol. Sci., Part A, Polymer Chemistry 25, 1093 (1987) and ACS, Polymer Prepr. 28, 92 (1987), Hergenrother et al. mention that 1,4-bis(4-fluorobenzoyl)benzene is accessible in the presence of AlCl3 from terephthaloyl chloride and fluorobenzene, but without going into experimental details. The yield according to these latter literature sources is a technically unsatisfactory 88% with a melting point of 218.5 to 219.5° C.

Our own investigations showed that, according to the AlCl3 process described above, the 1,4-bis(4-fluorobenzoyl)benzene is only obtained in a purity (see the Comparison Examples 3 and 6) which does not meet the high demands on starting compounds for high performance polymers. Under the conditions mentioned, i.e. during the Friedel-Crafts reaction, the fluorobenzene is converted into chlorobenzene by the AlCl3. This can also be verified in a model experiment in which the fluorobenzene is treated with AlCl3 at temperatures of about 85° C. (cf. Example 4). The chlorobenzene formed is enriched in excess fluorobenzene if this is not purified by complicated rectification before returning it. In the following reactions, this chlorobenzene inevitably reacts with terephthaloyl chloride analogously to fluorobenzene. A mixture of 1,4-bis(4-fluorobenzoyl)benzene, 1-(4-chlorobenzoyl)-4-(4-fluorobenzoyl)benzene and 1,4-bis(4-chlorobenzoyl)benzene is then obtained as the product, whose content of chlorine-containing bisbenzoylbenzenes increases with the amount of chlorobenzene in the fluorobenzene (cf. Examples 5 to 7).

This important fact for the preparation of fluorinated bisbenzoylbenzenes was not recognized in the preparation processes described hitherto and therefore also not taken into account, although nucleophilic polycondensation reactions to give polyether ketones or polyether ketosulfones, as is known, proceed more easily and selectively with fluoroaromatic compounds than with chlorinesubstituted aromatic compounds and the uniform chain synthesis by chlorine-containing substrates can thus be perturbed.

1-(2-Fluorobenzoyl)-4-(4-fluorobenzoyl)benzene can be detected as a further by-product in the abovementioned AlCl3 process. Using HPLC investigations, it can be shown that the content of the undesired isomer in the crude product amounts to about 4.4% by weight at a reaction temperature of about 85° C. This isomer has to be separated off in a complicated manner and then disposed of (cf. Example 3).

According to EP-OS 178,184 (see, in particular, Examples 4 to 6) and EP-OS 262,919, it is attempted to solve the problems shown by employing the Lewis acid employed as the catalyst in a relatively large excess and by modifying its activity by addition of a Lewis base. However, this means an additional waste water pollution beyond the requisite proportion. In addition, the isolated yields of at most 87% are industrially extremely unsatisfactory. The temperature of $\leq 0°$ C. used at the beginning of the reaction over the course of at least about ½ day necessitates a very high expenditure of cooling energy. The long reaction times of at least about 1 day are extremely disadvantageous for industrial use. The solvents dichloroethane or dichloromethane always used in EP-OS 178,184 (Examples 4 to 6) and EP-OS 262,919 are not acceptable toxicologically and on the industrial scale must be recycled in a complicated manner or disposed of.

Since for high quality applications of the plastics obtainable from the 1,4-bis(4-fluorobenzoyl)benzene as high a crystallinity as possible is required, the starting material employed for this purpose, in addition to a high general purity, must also have an isomeric purity of >99.5% For ecological and economic reasons (avoidance of waste substances which have to be disposed of), there was therefore a need to find a preparation process in which the content of secondary components in the crude product is as low as possible and a very high yield is attainable and amounts of AlCl3 and auxiliary components have to be employed which are as low as possible.

It has now surprisingly been found that, by the metering AlCl3 or AlBr3 into a mixture of fluorobenzene and terephthaloyl chloride at temperatures below 70° C., the formation of chlorobenzene or bromobenzene from fluorobenzene, as has to be expected according to Examples 4 and 6, can be virtually completely suppressed.

The invention therefore relates to a process for the preparation of 1,4-bis(4-fluorobenzoyl)benzene from terephthaloyl chloride and fluorobenzene in the presence of aluminum chloride or aluminum bromide at temperatures below 70° C. in very good yields by metering aluminum chloride or aluminum bromide into a mixture of terephthaloyl chloride and fluorobenzene at temperatures from about 25° C. to about 68° C., preferably from about 35° C. to about 65° C., and allowing the mixture to react.

The reduction of the reaction temperature from reflux conditions to temperatures below 70° C. leads to a clear reduction of the content of 1-(2-fluorobenzoyl)-4(4-fluorobenzoyl)benzene without the reaction times being considerably extended. However, it is possible in the case of virtually completed reaction to heat the reaction mixture to boiling temperature in order to drive off hydrogen chloride gas or to increase the fluidity of the reaction mixture without the isomer ratio being impaired.

Customarily, the fluorobenzene is employed in an amount of about 7 to about 20 mol, preferably of about 10 to about 16 mol per mol of terephthaloyl chloride. However, it is also possible to employ fluorobenzene in a higher excess, which, however, is no longer advantageous from economic considerations. The excess fluorobenzene can be recovered quantitatively.

AlCl$_3$ or AlBr$_3$ is employed in an amount of about 1.8 to about 3 mol, preferably about 1.9 to about 2.7 mol and particularly preferably about 2.0 to 2.5 mol, per mol of terephthaloyl chloride.

The reaction is carried out with the exclusion of atmospheric moisture, for example by blanketing with a protective gas atmosphere, at normal pressure, under reduced pressure (vacuum) or at elevated pressure.

Working-up is carried out in a manner known per se by hydrolysis of the reaction mixture, preferably by introducing the reaction mixture into water, and subsequent distillative removal of the excess fluorobenzene and removal of the solid reaction product from the aqueous phase. However, the crude product can also be removed first and then excess fluorobenzene can be recovered by phase separation.

The particular advantage of the process according to the invention is that 1,4-bis(4-fluorobenzoyl)benzene is already obtained as a crude product in a very high purity (the melting point of $\geq 220°$ C. is already higher by about 1° C. than in the product obtained by recrystallization according to U.S. Pat. No. 4,820,791) and virtually quantitative yield.

The content of 1-(2-fluorobenzoyl)-4-(4-fluorobenzoyl)benzene at a reaction temperature of 60° C. is only about 2.2% by weight instead of 4.4% by weight when the reaction is carried out under reflux conditions. The 1-(4-chlorobenzoyl)-4-(4-fluorobenzoyl)benzene or 1-(4-bromobenzoyl)-4-(4-fluorobenzoyl)benzene, which is scarcely separable by recrystallization (cf. Example 7), is not detectable in the crude product. Auxiliary reagents such as the addition of Lewis bases to the catalyst or the use of solvents are not necessary.

The fluorobenzene which is recovered by simple distillation or by phase separation can be reused directly after drying. A complicated rectification of the aromatic compound is not necessary, as virtually no chlorobenzene or bromobenzene is formed during the reaction. No enrichment of the fluorobenzene with chlorobenzene or bromobenzene can therefore take place during the recyclization. The formation of 1-(4-chlorobenzoyl)-4-(4-fluorobenzoyl)benzene and 1,4-bis(4-chlorobenzoyl)benzene or the corresponding monobromo and dibromo compounds can thus be excluded.

If the results of EP-OS 178,184 (cf. Example 7, reaction in dichloroethane as solvent in the presence of AlCl$_3$ at $-15°$ C. to room temperature, reaction time about 1 day, yield of 1,4-bis(4-fluorobenzoyl)benzene 83%, purity according to $^1$H-NMR 80%) are taken into account, it must be very particularly surprising that by metering in aluminum chloride with simultaneous reduction of the reaction temperature to values of less than about 70° C., the content of the poorly separable by-products 1-(2-fluorobenzoyl)-4-(4-fluorobenzoyl)benzene and 1-(4-chlorobenzoyl)-4-(fluorobenzoyl)benzene in the AlCl$_3$ process is clearly reduced and in spite of this a virtually quantitative yield is obtained.

Using the process according to the invention, an economical process for the preparation of 1,4-bis(4-fluorobenzoyl)benzene is available in that the crude product is already obtained in high purity and in nearly quantitative yield. The synthesis of the product in question can also be carried out on the industrial scale without a high and thus expensive outlay in terms of safety (cf. HF/BF$_3$ process according to DE-OS 3,806,656 and polyfluoroalkanesulfonic acid process according to DE-OS 3,807,623). The likewise cost-intensive rectification of fluorobenzene before recyclization can also be omitted.

The process according to the invention is illustrated in greater detail by the examples below, without being restricted thereto. The abbreviations included in the examples mean: Wt weight; GC gas chromatography; GC/MS=gas chromatography coupled with mass spectroscopy; GCSA=GC surface area; FID=flame ionization detector; HPLC=high pressure liquid chromatography; p,p-BFB=1,4-bis(4-fluorobenzoyl)benzene; o,p-BFB=1-(2-fluorobenzoyl)-4-(4-fluorobenzoyl)benzene; ClFB=1-(4-chlorobenzoyl)-4-(4-fluorobenzoyl)benzene; HA=4-(4-fluorobenzoyl)benzoic acid.

o,p-BFB and ClFB were prepared for comparison purposes by an independent route (Examples 8 and 9).

EXAMPLE 140.0 g of AlCl$_3$ are metered uniformly into a solution of 101.5 g of terephthaloyl chloride in 577 g of fluorobenzene at 60° C. in the course of 1.5 h. The mixture is subsequently stirred until evolution of gas is complete (about 2 h). The heterogeneous, intensively yellow reaction mixture is added to 1 l of water. Residues of the reaction mixture adhering in the reaction vessel are rinsed over using 102 g of fluorobenzene. 579 g (chlorobenzene content: about 0.001% by wt) of fluorobenzene are removed from the hydrolysis mixture by distillation. After removing the white precipitate, washing until neutral with 1 l of water and drying at 80° C./100 mbar, 160.1 g (99% of theory, based on terephthaloyl chloride) of 1,4-bis(4-fluorobenzoyl)benzene are obtained. Melting point 220° C.; content of o,p-BFB 2.2% by wt, HA 0.4% by wt, ClFB not detectable (HPLC, UV detection, external standard).

Thorough stirring with 2 N sodium hydroxide solution and recrystallization from chlorobenzene yields 154.0 g (96% of theory, based on terephthaloyl chloride) of 1,4-bis(4-fluorobenzoyl)benzene (content: >99.5% by wt; HPLC, external standard).

EXAMPLE 2

140.0 g of AlCl₃ are metered into a solution of 577 g of fluorobenzene and 101.5 g of terephthaloyl chloride at 25° C. to 30° C. over the course of 1.5 h. The mixture is stirred at 30° C. until evolution of gas is complete (about 3 h) and then worked up as described in Example 1. 154.9 g (96% of theory, based on terephthaloyl chloride) of 1,4-bis(4-fluorobenzoyl)benzene are obtained before the treatment with sodium hydroxide solution and recrystallization.

Melting point 221° C.; content of o,p-BFB 1.7% by wt

EXAMPLE 3 (COMPARISON EXAMPLE)

101.5 g of terephthaloyl chloride are reacted at 83° C. to 85° C. with 577 g of fluorobenzene and 140.0 g of AlCl₃ analogously to Example 2. The yield of crude product is 158.1 g.

Content of o,p-BFB 4.4% by wt.

EXAMPLE 4 (MODEL EXPERIMENT)

20 g of AlCl₃ are suspended in 100 g of fluorobenzene and the mixture is stirred at 85° C. to 90° C. for 5.5 h. According to GC/MS analysis of the volatile components, chlorobenzene (37% by SA, FID) and a number of other partly chlorine-containing, partly fluorine-containing conversion products of fluorobenzene are detected as reaction products in a total content of 25% in addition to fluorobenzene (38% by SA, FID).

EXAMPLE 5 (MODEL EXPERIMENT)

101.5 g of Terephthaloyl chloride are reacted at 60° C. to 85° C. with 288.3 g of fluorobenzene and 337.7 g of chlorobenzene and 140.0 g of AlCl₃ analogously to Example 2. 160.8 g of crude product are obtained which, according to 25.8% by wt of ClFB and 5 9% by wt of 1 4-bis(4-chlorobenzoyl)benzene.

EXAMPLE 6 (COMPARISON EXAMPLE)

101.5 g of terephthaloyl chloride are added dropwise at 70° C. to 75° C. to a mixture of 577 g of fluorobenzene and 140.0 g of AlCl₃. The mixture is stirred at this temperature until evolution of gas is complete and then worked up as described in Example 1. The yield of crude product is 157.9 g. Content of o,p-BFB 2.6% by wt, of ClFB 0.025% by wt, and of HA 0.5% by wt (HPLC, external standard).

The chlorobenzene content of the quantitatively recovered excess of fluorobenzene is 0.5% (GCSA).

EXAMPLE 7 (COMPARISON EXAMPLE)

01.5 g of terephthaloyl chloride are reacted at about 0° C. with 288.3 g of fluorobenzene (chlorobenzene content after repeated recycling of fluorobenzene without rectification (3.9% by GCSA, FID) analogously to Example 2. After working up analogously to Example 2 and thoroughly stirring with 2 N sodium hydroxide solution, 158.4 g of crude product are obtained which, in addition to p,p-BFB, still contain 2.2% by wt of o,p-BFB and 0.1% by wt of ClFB. Recrystallization from chlorobenzene yields p,p-BFB having an o,p-BFB content of 0.2% by wt and a ClFB content of 0.1% by wt (HPLC, external standard) in a yield of 95% of theory, based on terephthaloyl chloride.

EXAMPLE 8 (PREPARATION OF COMPARISON COMPOUND)

175 g of 4-chlorobenzoyl chloride are added dropwise at about 70° C. to a mixture of 553 g of toluene and 140 g of AlCl₃. After completion of the evolution of HCl, the reaction mixture is added to 1 l of water, and the solid obtained is separated off and recrystallized from 20 ethanol/toluene (50:1 parts by wt). 112.7 g of 4'-chloro-4-methylbenzophenone (melting point 129° C. to 130° C.; content of 4,4,-isomer >99.5% by GCSA) are obtained. 4-(4-Chlorobenzoyl)benzoic acid (melting point 256° C. to 258° C.) is accessible from this in 95% yield by oxidation. This acid is converted into the acid chloride by phosgenation. 97.7 g of 4-(4-chlorobenzoyl)benzoyl chloride, dissolved in 250.0 g of fluorobenzene, are added dropwise at 60° C. to 85° C. to a mixture of 254.5 g of fluorobenzene and 49.0 g of AlCl₃. After the evolution of gas is complete, the reaction mixture is added to 0.5 l of water and, after distillative removal of excess fluorobenzene, the precipitate is separated off, washed until neutral and recrystallized from chlorobenzene. Yield of 1-(4chlorobenzoyl-4-(4-fluorobenzoyl)benzene: 54.0 g (melting point 211° C. to 212° C.).

EXAMPLE 9 (PREPARATION OF COMPARISON COMPOUND)

A crude product is obtained in quantitative yield from 2-fluorobenzoyl chloride and toluene with AlCl₃ analogously to Example 8 and, according to GC, contains 90% of 2-fluoro-4'-methylbenzophenone, 8% pf the 2,2'-isomer and 2% of the 2,3'-isomer. Recrystallization from ethanol yields 2-fluoro-4'-methylbenzophenone of melting point 73° C. to 74° C. This compound si converted into the acid chloride analogously to Example 8, which acid chloride, with AlCl₃ in excess fluorobenzene, yields 1-(2-fluorobenzoyl)-4(4-fluorobenzoyl)benzene in 98% yield, based on 4-(2-fluorobenzoyl)benzoyl chloride (melting point 133° C.; purity according to HPLC: 97.4%). Further purification is possible by recrystallization from ethanol.

We claim:

1. A process for the preparation of 1,4-bis(4-fluorobenzoyl)benzene by reaction of terephthaloyl chloride with fluorobenzene in the presence of aluminum chloride or aluminum bromide, which comprises metering aluminum chloride or aluminum bromide into a mixture of terephthaloyl chloride and fluorobenzene at temperatures from about 25° C. to about 68° C. and allowing the mixture to react at said temperatures.

2. The process as claimed in claim 1, wherein the process is carried out at temperatures from about 35° C. to about 65° C.

3. The process as claimed in claim 1, wherein the aluminum chloride or aluminum bromide is employed in an amount of about 1.8 to about 3.0 mol per mol of terephthaloyl chloride.

4. The process as claimed in claim 1, wherein the aluminum chloride or aluminum bromide is employed in an amount of about 1.9 mol to about 2.7 mol per mol of terephthaloyl chloride.

5. The process as claimed in claim 1, wherein the aluminum chloride or aluminum bromide is employed in an amount of about 2.0 to about 2.5 mol per mol of terephthaloyl chloride.

6. The process as claimed in claim 1 wherein fluorobenzene is employed in an amount of about 7 mol to about 20 mol per mol of terephthaloyl chloride.

7. The process as claimed in claim 1 wherein the fluorobenzene is employed in an amount of about 10 mol to about 16 mol per mol of terephthaloyl chloride.

8. The process as claimed in claim 1 wherein the process is carried out at normal pressure, elevated pressure or reduced pressure (vacuum).

* * * * *